US012728198B2

(12) United States Patent
Schramm

(10) Patent No.: US 12,728,198 B2
(45) Date of Patent: Sep. 8, 2026

(54) MEDICAL DEVICE AND METHODS FOR ASSEMBLING AND DISASSEMBLING THE SAME

(71) Applicant: Roche Diabetes Care, Inc., Indianapolis, IN (US)

(72) Inventor: Rene Schramm, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 205 days.

(21) Appl. No.: 16/444,757

(22) Filed: Jun. 18, 2019

(65) Prior Publication Data

US 2019/0388612 A1 Dec. 26, 2019

(30) Foreign Application Priority Data

Jun. 22, 2018 (EP) .................................... 18179278

(51) Int. Cl.
*A61M 5/142* (2006.01)
*A61B 5/145* (2006.01)

(52) U.S. Cl.
CPC ..... *A61M 5/14244* (2013.01); *A61B 5/14532* (2013.01); *A61B 2560/0412* (2013.01); *A61B 2560/0431* (2013.01); *A61B 2560/0443* (2013.01); *A61B 2562/12* (2013.01); *A61M 2207/00* (2013.01); *A61M 2209/01* (2013.01)

(58) Field of Classification Search
CPC .... A61M 5/14244; A61M 5/142; A61B 90/08
See application file for complete search history.

(56) References Cited

U.S. PATENT DOCUMENTS

2004/0201512 A1 10/2004 Sugimoto et al.
2006/0166711 A1 7/2006 Schworm
2011/0194234 A1* 8/2011 Kim .................... H04M 1/0249 361/679.01
2012/0055838 A1 3/2012 Shinoda et al.
2014/0052055 A1 2/2014 Yodfat et al.
(Continued)

FOREIGN PATENT DOCUMENTS

WO WO 2011/046950 A1 4/2011
WO WO-2017190348 A1 * 11/2017 ........... G06F 1/1656

OTHER PUBLICATIONS

English Translation of WO2017190348A1 (Year: 2017).*
(Continued)

*Primary Examiner* — Charles A Marmor, II
*Assistant Examiner* — Severo Antonio P Lopez
(74) *Attorney, Agent, or Firm* — Bose McKinney & Evans LLP

(57) ABSTRACT

A medical device having a housing that includes a first housing part with a first sealing element and a second housing part with a second sealing element. The first housing part and the second housing part are releasably couplable to each other. The first housing part and the first sealing element are formed from a same first material and the second housing part and the second sealing element are formed from a same second material. The first sealing element forms at least one first protrusion and the second sealing element forms at least one second protrusion. Methods of assembling and disassembling such medical devices are also disclosed.

17 Claims, 5 Drawing Sheets

(56) References Cited

U.S. PATENT DOCUMENTS

2014/0207064 A1* 7/2014 Yavorsky ............ A61M 5/1413
604/151
2014/0268518 A1 9/2014 Huang et al.
2015/0005042 A1 1/2015 Lee et al.
2016/0213842 A1* 7/2016 Eggert .............. A61M 5/16831
2017/0351164 A1* 12/2017 Kim .................... H04M 1/0264

OTHER PUBLICATIONS

J. Hoenes et al.; The Technology Behind Glucose Meters: Test Strips; Diabetes Technology & Therapeutics, 2008; pp. S-10 to S-26; vol. 10, supp. 1.
Extended European Search Report, EP 18179278.9, Aug. 21, 2018, 9 pages.

* cited by examiner

MEDICAL DEVICE AND METHODS FOR ASSEMBLING AND DISASSEMBLING THE SAME

RELATED APPLICATIONS

This application claims priority to European Patent Application No. EP 18 179 278.9, filed Jun. 22, 2018, the entire disclosure of which is hereby incorporated herein by reference.

BACKGROUND

This disclosure relates to a medical device such as a medical pump, specifically an insulin pump; a remote control unit of a medical pump or a handheld medical measurement device, specifically a handheld blood glucose measurement device. Further, this disclosure relates to a method for disassembling at least one medical device and to a method for assembling at least one medical device. The method and devices according to the present disclosure may mainly be used for delivering insulin to a user or a patient and/or for conducting at least one analytical measurement of a body fluid of the user or the patient. This disclosure may both be applied in the field of home care as well as in the field of professional care, such as in hospitals. Other applications are generally feasible.

Delivering medicine to a user, specifically insulin delivery, plays an important role in the prevention and treatment of diseases, in particular in the treatment of diabetes mellitus. Besides using injection pens or syringes, insulin delivery may specifically be performed by using insulin pumps.

In particular, a user is generally required to wear the insulin pump on his or her body at all times, thus leading to a preferably small and compact construction of the insulin pump and its components. Common pumps for delivering medicine, such as, for example, insulin, comprise a plurality of medicine reservoirs. As an example, fluid delivery devices are disclosed in WO2011/046950 A1. The fluid delivery device comprises a housing having a fluid reservoir. A needle is in fluid communication with the fluid reservoir in an engaged position and out of fluid communication with the fluid reservoir in armed and storage positions. A proximal end of a biasing member is coupled to the housing and a distal end of the biasing member is configured to deliver a force to the fluid reservoir. A piston member extends through the biasing member and is coupled to the distal end of the biasing member. The piston member is fixed with respect to the housing in a locked position such that the biasing member does not deliver the force to the fluid reservoir and the piston member is moveable with respect to the housing in a released position such that the biasing member delivers the force to the fluid reservoir. Transitioning the needle from the storage position to the armed position transitions the piston from the locked position to the released position.

Further, in the field of medical technology and diagnostics, a large number of devices and methods for determining the presence and/or the concentration of one or more analytes in samples, specifically fluid samples, such as body fluids, and/or for determining at least one parameter of a sample are known. For performing fast and simple measurements, several types of test elements are known, which mainly are based on the use of one or more test chemicals, i.e. on the use of one or more chemical substances, one or more chemical compounds or one or more chemical mixtures, adapted for performing a detection reaction for detecting the analyte or determining the parameter. The test chemical often is also referred to as a test substance, a test reagent, a test chemistry or as a detector substance. For details of potential test chemicals and test elements comprising such test chemicals, which may also be used within the present disclosure, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present disclosure.

Commonly, medical pumps, remote control units of medical pumps, handheld medical measurement devices or other medical devices comprise electrical components. Specifically, medical pumps, remote control units of medical pumps, handheld medical measurement devices or other medical devices may require energy sources such as batteries or accumulators. These energy sources typically have to be exchanged by a patient or a user frequently. Thus, a compartment of the medical device for storing the energy sources has to be designed in an accessible manner. Therefore, the compartment is prone to get dirty and to receive water and other fluids. This may create the risk that a functionality of the energy source, and thus of the whole medical device, is not available any more. Thus, a required standard of water proofing has to be achieved. As a consequence, measures have to be taken to seal the compartment from an ambient environment.

Despite the advantages of state of the art pumps for delivering insulin and handheld medical measurement devices several technical challenges remain. 2K (two-component) molded sealing parts are commonly expensive. Further, 2K molded sealing parts typically imply several technical challenges. Thus, after contact with one or more of water, dust and dirt; one or more of water, dust and dirt may penetrate an interior of the housing, specifically the battery compartment, which may cause errors within the medical device. This may lead to an unreliable measurement result. Further, 2K molded sealing parts commonly show an increased risk of abrasion. Further, the manufacturing process may be time-consuming and expensive.

SUMMARY

The present disclosure provides a medical device, a method for disassembling at least one medical device and a method for assembling at least one medical device, which at least partially avoid the shortcomings of known devices and methods of this kind and which at least partially address the above-mentioned challenges. Specifically, devices and methods are disclosed which allow for easy manufacturing and simple handling processes by a user.

As used in the following, the terms “have”, “comprise” or “include” or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions “A has B”, “A comprises B” and “A includes B” may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms “at least one”, “one or more” or similar expressions indicating that a feature or element may be present once or more than once typically will be used only once when introducing the respective feature or element. In the following, in most cases, when referring to the respective feature or element, the expressions “at least one” or “one or more” will not be repeated, notwithstanding the fact that the respective feature or element may be present once or more than once.

Further, as used in the following, the terms “preferably”, “more preferably”, “particularly”, “more particularly”, “specifically”, “more specifically” or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by “in an embodiment of the invention” or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first embodiment, a medical device is disclosed. The medical device comprises at least one housing. The housing comprises at least one first housing part. The first housing part comprises at least one first sealing element. The housing comprises at least one second housing part. The second housing part comprises at least one second sealing element. The first housing part and the second housing part are releasably couplable to each other. Further, the first housing part and the second housing part are configured to form at least one coupled state. The first housing part and the first sealing element are formed from a same first material. The second housing part and the second sealing element are formed from a same second material. The first sealing element forms at least one first protrusion and the second sealing element forms at least one second protrusion.

The term “medical device” as used herein is a broad term and is to be given its ordinary and customary meaning to a person of ordinary skill in the art and is not to be limited to a special or customized meaning. Without limitation, medical device, therefore, generally may be an arbitrary device configured for performing at least one therapeutic purpose. The medical device specifically may comprise one component or an assembly of two or more components capable of interacting with each other, such as in order to perform one or more therapeutic purposes, such as in order to perform a medical procedure. The medical device generally may also be, or may comprise, at least one of a medical system or a medical kit. The medical device generally may be used for delivering at least one medication such as a drug and/or a therapeutic agent to a user. Thus, the medical device may be used as part of one or more medical treatments.

The medical device may, for example, be selected from the group consisting of: a medical pump, specifically an insulin pump; a remote control unit of a medical pump; a handheld medical measurement device, specifically a handheld blood glucose measurement device. The handheld medical measurement device may have a receptacle for receiving, at least partially, at least one test element such as a test strip. Thus, the handheld medical measurement device may be configured to conduct at least one analytical measurement on a test field of the test element and to derive at least one item of information from the analytical measurement which relates to a health status of a user or a patient. However, other embodiments of the medical device may also be feasible.

The terms “patient” and “user” as used herein are broad terms and are to be given their ordinary and customary meaning to a person of ordinary skill in the art and are not to be limited to a special or customized meaning. The terms may refer, without limitation, to a human being or an animal, independent from the fact that the human being or animal, respectively, may be in a healthy condition or may suffer from one or more diseases. As an example, the patient or the user may be a human being or an animal suffering from diabetes. However, additionally or alternatively, this disclosure may be applied to other types of users or patients or diseases.

The housing may comprise at least one compartment, specifically at least one battery compartment. The term “compartment” as used herein is a broad term and is to be given its ordinary and customary meaning to a person of ordinary skill in the art and is not to be limited to a special or customized meaning. The term specifically may refer, without limitation, to an arbitrary interior space of an object. Specifically, the interior space may be covered by one or more components or parts of the object. The interior space may be configured for receiving and/or storing another element. The element may have a shape which is complementary to a shape of the interior space.

The term “battery compartment” as used herein is a broad term and is to be given its ordinary and customary meaning to a person of ordinary skill in the art and is not to be limited to a special or customized meaning. The term specifically may refer, without limitation, to an arbitrary compartment which is configured for receiving a battery and/or an accumulator. The battery compartment may have one or more electrical contacts configured for establishing at least one electrical connection to the battery or the accumulator. The first housing part and the second housing part may be configured for enclosing the battery compartment as will further be described below in more detail. Specifically, the second housing part may be a battery compartment lid. Thus, the second housing part may be configured to be reversibly removable from the first housing part in order to exchange the battery and/or the accumulator.

The first housing part may also contain at least one open compartment receiving at least one electrical component, specifically at least one battery and/or accumulator. The term “open compartment” as used herein is a broad term and is to be given its ordinary and customary meaning to a person of ordinary skill in the art and is not to be limited to a special or customized meaning. The term specifically may refer, without limitation, to an arbitrary compartment which is accessible from at least one side of the compartment. For example, the compartment may have several sidewalls and a bottom. However, a top side of the compartment may be open. Thus, the top side may be referred to as an open side. However, the open side may be coverable with a further element such as a cover. The second housing part, in the coupled state, may cover the open compartment.

The compartment may comprise electrical contacts in at least one sidewall of the compartment for contacting the electrical component. In the coupled state, the first and second sealing elements may be located at least on a side of the compartment adjacent to the side wall having the electrical contacts. Further, the compartment may have a rectangular shape. The second housing part may be configured for being slid onto the first housing part in a sliding direction parallel to at least one side of the rectangular shape. The sliding direction may be at least essentially parallel to the longer side of the rectangular shape. Further, the first and second protrusions may be arranged on a side upstream the rectangular shape with respect to the sliding direction.

The term "housing" as used herein is a broad term and is to be given its ordinary and customary meaning to a person of ordinary skill in the art and is not to be limited to a special or customized meaning. The term specifically may refer, without limitation, to an element or component having at least one interior space and at least one wall of fully or partially surrounding the at least one interior space and providing protection to the interior space, such as one or more of a mechanical protection or a protection against environmental influences such as one or more of moisture, oxygen or microbial contaminations. The housing may generally be adapted to fully or partially surround and/or receive one or more elements in order to provide one or more of a mechanical protection, a mechanical stability, an environmental protection against moisture and/or ambient atmosphere. The housing may also provide a basis for attachment and/or holding one or more further components or elements.

The term "part" as used herein is a broad term and is to be given its ordinary and customary meaning to a person of ordinary skill in the art and is not to be limited to a special or customized meaning. The term specifically may refer, without limitation, to an arbitrary component of an object. The component may be configured for interacting with a further component of the object. Specifically, the first housing part and the second housing part may be capable of interacting with each other, such as in order to perform one or more purposes, such as in order to shield an interior space of the first housing part.

The terms "first housing part" and "second housing part" may be considered as nomenclature only, without numbering or ranking the named elements, without specifying an order and without excluding a possibility that several kinds of first housing parts and second housing parts may be present. Further, additional housing parts, such as one or more third housing parts, may also be present As further used herein, the term "releasable", in the context of a mechanical connection, generally refers to the fact that the mechanical connection may be brought from a disconnected state, also referred to as a non-mated state, into a connected state, also referred to as a mated state, and back into the disconnected state. Thus, the mechanical connection may be closed and released at will. Specifically, the mechanical connection may be releasable without using any tools, simply by manual action. As an example, for opening a connection between the first housing part and the second housing part, forces of no more than 50 N, of no more than 20 N, or of no more than 10 N, may be required, which may be applied by one hand or even the fingers or fingertips of the user.

The term "couplable" as used herein is a broad term and is to be given its ordinary and customary meaning to a person of ordinary skill in the art and is not to be limited to a special or customized meaning. The term specifically may refer, without limitation, to a property of one or more components which are configured to be brought from a disconnected state, also referred to as a non-mated state, into a connected state, also referred to as a mated state or referred to as a coupled state, and back into the disconnected state. In the disconnected state, the components may be completely disassembled, e.g. the components may be arranged at a distance from each other and may not be in contact with each other. However, alternatively, in the disconnected state, a contact between the components may remain. For example, a first end of a first component may stay connected to a second end of a second component. In the coupled state, the components may be configured to form an interior space. One or more elements may be received in the interior space. Thus, the term "coupled state", as further used herein, may refer to an assembled state of the first housing part and the second housing part. The coupling, specifically, may take place by a form-fit and/or force-fit connection, e.g. by a connection via one or more interacting or complementary coupling elements on the parts to be coupled, such as a sliding connection and/or a snap-fit connection. Examples will be given in further detail below.

The first housing part and the second housing part may be configured to establish at least one mechanical connection, specifically a form-fit connection. As used herein, the term "mechanical connection" generally refers to a connection of two or more components by mechanical holding forces.

The term "sealing element" as used herein is a broad term and is to be given its ordinary and customary meaning to a person of ordinary skill in the art and is not to be limited to a special or customized meaning. The term specifically may refer, without limitation, to an arbitrary element which is configured to fully or partially conceal at least one opening and/or to fully or partially surround one or more objects to be sealed off from environmental influences such as moisture, dust and/or dirt. Specifically, the sealing element may be configured to at least partially surround the at least one element to be sealed off from the environmental influences in at least two dimensions.

The terms "first sealing element" and "second sealing element" may be considered as nomenclature only, without numbering or ranking the named elements, without specifying an order and without excluding a possibility that several kinds of first sealing elements and second sealing elements may be present. Further, additional sealing elements such as one or more third sealing elements may be present. Specifically, the first housing part may comprise at least two of the first sealing elements, preferably at least three of the first sealing elements, more preferably at least four of the first sealing elements. Further, the second housing part may comprise at least two of the second sealing elements, preferably at least three of the second sealing elements, more preferably at least four of the second sealing elements. However, other embodiments, such as a larger number of first sealing elements and second sealing elements, may also be feasible. A number of the first sealing elements and a number of second sealing elements may be identical.

One or both of the first material and the second material may be selected from the group consisting of: a thermoplastic material, specifically a thermoplastic compound comprising polycarbonate and acrylonitrile butadiene styrene. Specifically, at least one element selected from the group consisting of: the first housing part, the second housing part, the first sealing element, the second sealing element, may be manufactured via injection molding. The first housing part and the first sealing element may be manufactured as one piece, specifically via injection molding. The second housing part and the second sealing element may be manufactured as one piece, specifically via injection molding. Specifically, all elements selected from the group consisting of the first housing part, the second housing part, the first sealing element and the second sealing element may be manufactured without using elastomeric components, such as rubber materials, e.g., by using rigid thermoplastic materials only.

The term "protrusion" as used herein is a broad term and is to be given its ordinary and customary meaning to a person of ordinary skill in the art and is not to be limited to a special or customized meaning. The term specifically may refer, without limitation, to an arbitrary element or part of an object which protrudes from a surface of the object. The terms "first protrusion" and "second protrusion" may be considered as nomenclature only, without numbering or ranking the named elements, without specifying an order and without excluding a possibility that several kinds of first protrusions and second protrusions may be present. Further, additional protrusions such as one or more third protrusions may be present.

The first protrusion may have a first shape and the second protrusion may have a second shape. The first shape may be identical to the second shape. Alternatively, the first shape and the second shape may differ from each other. A cross-section of the first protrusion and/or of the second protrusion, specifically a cross-section along a sliding direction of the medical device, as will further be described below, may be triangularly formed. However, other shapes may be feasible. The first protrusion may extend from a surface of the first housing part and may be tapered. Thus, the first protrusion may have a first tip which extends transverse, specifically perpendicular, to the surface of the first housing part. The first tip may point to a surface of the second housing part and may specifically be in direct contact with the surface of the second housing part. The second protrusion may extend from a surface of the second housing part and may be tapered. Thus, the second protrusion may have a second tip which extends transverse, specifically perpendicular, to the surface of the second housing part. The second tip may point to a surface of the first housing part and may specifically be in direct contact with the surface of the first housing part.

The first protrusion and/or the second protrusion may have a width of 0.1 mm to 0.8 mm, preferably of 0.2 mm to 0.6 mm, more preferably of 0.3 mm to 0.4 mm. Further, the first protrusion and/or the second protrusion may have a height of 0.01 mm to 0.5 mm, preferably of 0.05 mm to 0.3 mm, more preferably of 0.1 mm to 0.2 mm. Specifically, a height of the first protrusion may be identical to a height of the second protrusion. However, alternatively, the height of the first protrusion may differ from the height of the second protrusion.

As described above, the first housing part and the second housing part may be arranged in the coupled state. In the coupled state of the first housing part and the second housing part, the first sealing element of the first housing part and the second sealing element of the second housing part may be arranged offset in relation to each other. The term "arranged offset in relation to each other" as used herein is a broad term and is to be given its ordinary and customary meaning to a person of ordinary skill in the art and is not to be limited to a special or customized meaning. The term specifically may refer, without limitation, to an arrangement of a first element and of a second element relative to each other, wherein the first element is located in a first position relative to a reference point, wherein the second element is located in a second position relative to the reference point, wherein the first position is different from the second position. Thus, the first element and the second element may be arranged at a distance from each other. Further, the first element and the second element may be contact-free, e.g. the first element and the second element may be spaced apart from each other. However, an area of the first element may also be in direct contact with the second element.

Further, in the coupled state of the first housing part and the second housing part, the first sealing element of the first housing part and the second sealing element of the second housing part may form an intermediate space. The term "intermediate space" as used herein is a broad term and is to be given its ordinary and customary meaning to a person of ordinary skill in the art and is not to be limited to a special or customized meaning. The term specifically may refer, without limitation, to a free volume or empty space between a first element and a second element. The intermediate space may thus also be referred to as a gap. The intermediate space may be surrounded by one or more surfaces of the first element and the second element. Thus, the intermediate space may be at least partially, e.g. fully or partially, surrounded by the one or more surfaces of the first element and the second element. The gap may be a closed gap. Thus, the intermediate space may be fully surrounded by one or more surfaces of the first element and the second element. Specifically, the intermediate space may be formed by at least one surface of the first protrusion, at least one surface of the second protrusion, the at least one surface of the first housing part and the at least one surface of the second housing part. The intermediate space may be configured for receiving one or more of fluid, dust, dirt from an outer environment of the medical device.

Further, in the coupled state of the first housing part and the second housing part the first sealing element and the second sealing element may be arranged parallel to each other. The term "parallel" as used herein is a broad term and is to be given its ordinary and customary meaning to a person of ordinary skill in the art and is not to be limited to a special or customized meaning. The term specifically may refer, without limitation, to an arrangement of two or more elements, wherein the two or more elements extend in a same direction. For example, the first sealing element and/or the second sealing element may have curved shape, e.g. the first sealing element extends along the surface of the first housing part deviating from a straight line and/or, e.g., the second sealing element extends along the surface of the second housing part deviating from a straight line. As further used herein, the term "curved shape" may refer to a shape of an arbitrary object, wherein an extension of the object deviates from a straight line. Thus, parts of the object such as one end of the object may be arranged in an angle relative to a major axis. Specifically, the object may have an angle of 30° to 60°, preferably of 40° to 45°, more preferably of 45°, to the major axis. Thereby, the object may preferably be, at least to a large extent, free from bends. In case the first sealing element has a curved shape, the second sealing element may also have a curved shape as well. The curved shape of the first sealing element may correspond to the curved shape of the second sealing element. Specifically, the curved shape of the first sealing element may be identical to the curved shape of the second sealing element.

The first sealing element may be arranged along at least one side of the first housing part such as on a face side of the first housing part. Correspondingly, the second sealing element may be arranged along at least one side of the second housing part such as on a face side of the second housing part. However, other embodiments may be feasible. For example, the first sealing element and the second sealing element may respectively form at least one circumferential line on the first housing part and the second housing part.

The first housing part may comprise at least one first sealing surface, preferably at least one flat first sealing surface, and, in the coupled state of the first housing part and the second housing part, the second sealing element may seal against the first sealing surface. Further, the second housing part may comprise at least one second sealing surface, preferably at least one flat second sealing surface, and, in the coupled state of the first housing part and the second housing part, the first sealing element may seal against the second sealing surface.

Specifically, as described above, the first and second sealing surfaces may be flat sealing surfaces. The first protrusion may protrude from, e.g. extend from, the first sealing surface and the second protrusion may protrude from the second sealing surface. The first protrusion may seal against the second sealing surface along at least one first sealing line and the second protrusion may seal against the first sealing surface along at least one second sealing line. The first and second sealing lines may be offset from one another. The term "sealing line" as further used herein may refer to an arbitrary line along a surface of the first housing part or of the second housing part along which the first sealing element or second sealing element is arranged and extends.

The first and second sealing surfaces may be offset from one another, thereby forming a gap between the first and second sealing surfaces. The first protrusion may protrude from the first sealing surface by a first height and the second protrusion may protrude from the second sealing surface by a second height. The first height and the second height may be equal. Further, the width of the gap may correspond to the first and second heights.

The second housing part may form a sliding lid of the housing. The term "lid" as used herein is a broad term and is to be given its ordinary and customary meaning to a person of ordinary skill in the art and is not to be limited to a special or customized meaning. The term specifically may refer, without limitation, to a removable cover for closing and/or sealing an opening of an arbitrary object. Specifically, the lid may be arranged at a top of the housing. The lid may have a shape that corresponds to a shape of the opening. The term "sliding lid" as used herein is a broad term and is to be given its ordinary and customary meaning to a person of ordinary skill in the art and is not to be limited to a special or customized meaning. The term specifically may refer, without limitation, to an arbitrary lid which is removable from another object via a least one sliding mechanism. The term "sliding mechanism" is further described below in more detail. Specifically, the first sealing element and the second sealing element may respectively extend transverse, specifically perpendicular, to a sliding direction of the second housing part. As described above, the first sealing element and/or the second sealing element may have a curved shape. Thus, for example, one section of the first sealing element may be arranged at an angle of 90° to the sliding direction and another section of the first sealing element may be arranged at an angle deviating from 90° to the sliding direction such as at an angle of 20° to 70°, preferably at an angle of 30° to 60°, to the sliding direction.

The first housing part or the second housing part may additionally comprise at least one groove. The groove may be configured for collecting fluids. The term "groove" as used herein is a broad term and is to be given its ordinary and customary meaning to a person of ordinary skill in the art and is not to be limited to a special or customized meaning. The term specifically may refer, without limitation, to a receptacle or a slot on a surface of an arbitrary element. The groove may be configured for receiving at least one other element. Specifically, the groove may be configured for receiving at least one of fluid, specifically water, dust, dirt. The groove may have a width of 0.1 mm to 1 mm, preferably of 0.2 mm to 0.8 mm, more preferably of 0.5 mm to 0.7 mm. Further, the groove may have a depth of 0.05 mm to 0.5 mm, preferably of 0.1 mm to 0.4 mm, more preferably of 0.2 mm to 0.3 mm.

The groove may be arranged on a surface of the first housing part or on a surface of the second housing part. Thus, the groove may be arranged adjacent to the first sealing element or adjacent to the second sealing element. Specifically, the groove may be adjacent to one or both of the first protrusion and the second protrusion. Further, the groove may be arranged adjacent to the intermediate space formed by the first sealing element and the second sealing element as described above. Specifically, the groove may be at least partially parallel to one or both of the first protrusion and the second protrusion. The first housing part and the second housing part, in the coupled state, may enclose the intermediate space within the medical device and the groove may be arranged on a side of the first and second sealing elements facing towards the intermediate space.

The housing may comprise at least one linear sliding mechanism. The term "linear sliding mechanism" as used herein is a broad term and is to be given its ordinary and customary meaning to a person of ordinary skill in the art and is not to be limited to a special or customized meaning. The term specifically may refer, without limitation, to an arbitrary mechanism which is based on a linear sliding movement of two or more components relative to each other. The term "sliding movement" may refer to a movement along a continuous connection with another element, specifically with a surface, more specifically a smooth surface, of the other element. Specifically, the linear sliding mechanism may comprise one or more interacting sliding elements, such as one or more guide rails or the like. Further, the term "linear sliding movement" may generally refer to a movement along a straight line, e.g. within two dimensions.

The first housing part may comprise at least one sliding receptacle and the second housing part may comprise at least one sliding guide rail or vice versa. The sliding receptacle and the sliding guide rail in conjunction may form a sliding connector configured for establishing a releasable mechanical connection between the first housing part and the second housing part. As further used herein, the terms "sliding receptacle" and "sliding guide rail" may refer to elements which are complementary to each other and which are configured to interact with each other in order to realize the linear sliding mechanism. For example, the sliding guide rail may be formed as a protrusion. However, other embodiments may be feasible. The sliding guide rail and the sliding receptacle may be shaped complementary to each other. For example, the sliding receptacle and the guide rail may have an elongate shape and may extend along a longitudinal axis of the medical device. The term "sliding connector", also referred to as a sliding connection, may generally refer to an arbitrary connector or connection between two linear sliding contours. Therein, generally, one or both of the linear sliding contours involved may comprise at least one protrusion and, in a complementary fashion, the other one of the linear sliding contours may comprise at least one linear sliding grove or linear sliding slot in which the protrusion may be guided in order to form the linear sliding connection or linear sliding connector. The first part and the second part may be configured to establish at least one mechanical connection, specifically a form-fit connection. As used herein, the term "mechanical connection" generally refers to a connection of two or more components by mechanical holding forces. The housing may comprise at least one face side and at least one longitudinal side. The first sealing element and the second sealing element may be arranged along the face side and the sliding receptacle and the sliding guide rail may be arranged along the longitudinal side.

The housing may further comprise at least one latching mechanism. The term "latching mechanism" as used herein is a broad term and is to be given its ordinary and customary meaning to a person of ordinary skill in the art and is not to be limited to a special or customized meaning. The term specifically may refer, without limitation, to an arbitrary mechanism which is based on a linear sliding movement of two or more components relative to each other and wherein a movement of one component relative to another component is allowed in at least one direction, but is blocked in at least one counter direction. The first housing part may comprise at least one latching receptacle and the second housing part may comprise at least one latching protrusion or vice versa. The latching receptacle may be configured for receiving and fixing the latching protrusion. Thus, the latching protrusion may be removable from the latching receptacle by applying a force to the second housing part relative to the first housing part in the sliding direction. However, when applying a force to the second housing part in a counter direction, a movement of the second housing part relative to the first housing part may be blocked. The first sealing element and the second sealing element may be arranged transverse to the sliding receptacle and the sliding guide rail.

In a further aspect of the present disclosure, a method for disassembling at least one medical device is disclosed. The method for disassembling at least one medical device may include the method steps listed below. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for disassembling at least one medical device comprises the following steps:

a) providing at least one medical device as described above or as will further be described below in more detail wherein the first housing part and the second housing part are in the coupled state;
b) pushing the second housing part relative to the first housing part, thereby removing one or more of water, dust, dirt from a gap between the first housing part and the second housing part via the second sealing element.

As described above, the medical device may further comprise the at least one groove. The groove may be configured to receive one or more of fluid, specifically water, dirt, dust, prior to pushing the second housing part relative to the first housing part.

In a further aspect of the present disclosure, a method for assembling at least one medical device is disclosed. The medical device may correspond to the medical device as described above or as will further be described below in more detail.

The method for assembling at least one medical device comprises the method steps as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method for assembling at least one medical device comprises the following steps:

I. providing at least one first housing part, wherein the first housing part comprises at least one first sealing element, wherein the first housing part and the first sealing element are formed from a same first material, wherein the first sealing element forms at least one first protrusion;
II. providing at least one second housing part, wherein the second housing part comprises at least one second sealing element, wherein the second housing part and the second sealing element are formed from a same second material, wherein the second sealing element forms at least one second protrusion;
III. releasably coupling the first housing part and the second housing part to each other such that the first housing part and the second housing part form a coupled state.

One or both of the first housing part, the second housing part, may be manufactured via injection molding. Further, the first housing part and the first sealing element may be manufactured as one piece. Additionally or alternatively, the second housing part and the second sealing element may be manufactured as one piece.

The proposed medical device and the proposed method for disassembling at least one medical device provide many advantages over known devices and methods. Thus, an improved sealing for a medical device may be provided. The second housing part, specifically the battery lid, may require a sealing to prevent fluids, such as water, to ingress up to a certain level.

2K molded sealing parts are commonly expensive. Further, as outlined above, 2K molded sealing parts may imply several technical challenges. Thus, after contact with one or more of water, dust, dirt; one or more of water, dust, dirt may penetrate an interior of the housing, specifically the battery compartment, which may cause errors within the medical device and may lead to an unreliable measurement result.

It turned out that a plurality of retaining means, specifically the first sealing element and the second sealing element, is generally sufficient to reach a required standard of water proofing. A special advantage may be that the material of the sealing elements may be identical to the material of the housing parts. Thus, fluids, dust and dirt may be received and stripped off prior to reaching the interior compartment of the housing, specifically electrical contacts received in the housing.

Further, the medical device may have the receptacle as described above and as will further be described below in more detail. Thus, water which reaches an interior space of the first housing part and the second housing part may be received and prevented from reaching the interior compartment, specifically the electrical contacts of the interior compartment and specifically the battery received in the interior compartment.

As further advantages, an abrasion of the first sealing element and the second sealing element is avoided or at least prevented to a large extent. Further, production costs may be reduced as an application of an additional 2K molding procedure is avoided and an additional mounting step can be omitted. Further, the first sealing element and the second sealing element do not have to be tested Further, the user or the patient may be able to open the housing, specifically to remove the second housing part from the first housing part, by themselves in an easy manner, specifically without the necessity to twist screws on and off.

Summarizing and without excluding further possible embodiments, the following embodiments may be envisaged:

Embodiment 1

A medical device, wherein the medical device comprises at least one housing, wherein the housing comprises:

at least one first housing part, wherein the first housing part comprises at least one first sealing element;

at least one second housing part, wherein the second housing part comprises at least one second sealing element;

wherein the first housing part and the second housing part are releasably couplable to each other and may form at least one coupled state, wherein the first housing part and the first sealing element are formed from a same first material, wherein the second housing part and the second sealing element are formed from a same second material, wherein the first sealing element forms at least one first protrusion and wherein the second sealing element forms at least one second protrusion.

Embodiment 2

The medical device according to the preceding embodiment, wherein the first housing part comprises at least one first sealing surface, preferably at least one flat first sealing surface, wherein, in the coupled state of the first housing part and the second housing part, the second sealing element seals against the first sealing surface, wherein the second housing part comprises at least one second sealing surface, preferably at least one flat second sealing surface, wherein, in the coupled state of the first housing part and the second housing part, the first sealing element seals against the second sealing surface.

Embodiment 3

The medical device according to the preceding embodiment, wherein the first and second sealing surfaces are flat sealing surfaces, wherein the first protrusion protrudes from the first sealing surface and wherein the second protrusion protrudes from the second sealing surface.

Embodiment 4

The medical device according to any one of the two preceding embodiments, wherein the first protrusion seals against the second sealing surface along at least one first sealing line, wherein the second protrusion seals against the first sealing surface along at least one second sealing line, wherein the first and second sealing lines are offset from one another.

Embodiment 5

The medical device according to any one of the three preceding embodiments, wherein the first and second sealing surfaces are offset from one another, thereby forming a gap between the first and second sealing surfaces.

Embodiment 6

The medical device according to the preceding embodiment, wherein the first protrusion protrudes from the first sealing surface by a first height, wherein the second protrusion protrudes from the second sealing surface by a second height, wherein the first height and the second height are equal, wherein the width of the gap corresponds to the first and second heights.

Embodiment 7

The medical device according to any one of the preceding embodiments, wherein in the coupled state of the first housing part and the second housing part, the first sealing element of the first housing part and the second sealing element of the second housing part are arranged offset in relation to each other.

Embodiment 8

The medical device according to any one of the preceding embodiments, wherein in the coupled state of the first housing part and the second housing part, the first sealing element of the first housing part and the second sealing element of the second housing part form an intermediate space.

Embodiment 9

The medical device according to any one of the preceding embodiments, wherein in the coupled state of the first housing part and the second housing part the first sealing element and the second sealing element are arranged at least partially parallel to each other.

Embodiment 10

The medical device according to any one of the preceding embodiments, wherein the first housing part contains at least one open compartment receiving at least one electrical component, specifically at least one battery and/or accumulator, wherein the second housing part, in the coupled state, covers the open compartment.

Embodiment 11

The medical device according to the preceding embodiment, wherein the compartment comprises electrical contacts in at least one sidewall of the compartment, for contacting the electrical component, wherein, in the coupled state, the first and second sealing elements are located at least on a side of the compartment adjacent to the side wall having the electrical contacts.

Embodiment 12

The medical device according to any one of the preceding embodiments, wherein the second housing part forms a sliding lid of the housing.

Embodiment 13

The medical device according to the preceding embodiment, wherein the first sealing element and the second sealing element respectively extend transverse to a sliding direction of the second housing part.

Embodiment 14

The medical device according to any one of the preceding embodiments, wherein a cross-section of the first protrusion and/or of the second protrusion is triangularly formed.

Embodiment 15

The medical device according to any one of the preceding embodiments, wherein the first protrusion and/or the second protrusion have a width of 0.1 mm to 0.8 mm, preferably of 0.2 mm to 0.6 mm, more preferably of 0.3 mm to 0.4 mm.

Embodiment 16

The medical device according to any one of the preceding embodiments, wherein the first protrusion and/or the second protrusion have a height of 0.01 mm to 0.5 mm, preferably of 0.05 mm to 0.3 mm, more preferably of 0.1 mm to 0.2 mm.

Embodiment 17

The medical device according to any one of the preceding embodiments, wherein the first housing part or the second housing part additionally comprises at least one groove, wherein the groove is configured for collecting fluids.

Embodiment 18

The medical device according to the preceding embodiments, wherein the groove has a width of 0.1 mm to 1 mm, preferably of 0.2 mm to 0.8 mm, more preferably of 0.5 mm to 0.7 mm.

Embodiment 19

The medical device according to any one of the two preceding embodiments, wherein the groove has a depth of 0.05 mm to 0.5 mm, preferably of 0.1 mm to 0.4 mm, more preferably of 0.2 mm to 0.3 mm.

Embodiment 20

The medical device according to any one of the three preceding embodiments, wherein the groove is adjacent to one or both of the first protrusion and the second protrusion.

Embodiment 21

The medical device according to any one of the four preceding embodiments, wherein the groove is at least partially parallel to one or both of first protrusion and the second protrusion.

Embodiment 22

The medical device according to any one of the five preceding embodiments, wherein the first housing part and the second housing part, in the coupled state, enclose an intermediate space within the medical device, wherein the intermediate space is arranged on a side of the first and second sealing elements facing towards the intermediate space.

Embodiment 23

The medical device according to any one of the preceding embodiments, wherein the first housing part comprises at least two of the first sealing elements, preferably at least three of the first sealing elements, more preferably at least four of the first sealing elements and wherein the second housing part comprises at least two of the second sealing elements, preferably at least three of the second sealing elements, more preferably at least four of the second sealing elements.

Embodiment 24

The medical device according to any one of the preceding embodiments, wherein the first sealing element and the second sealing element respectively form at least one circumferential line on the first housing part and the second housing part.

Embodiment 25

The medical device according to any one of the preceding embodiments, wherein the housing comprises at least one sliding mechanism, specifically at least one linear sliding mechanism, wherein the first housing part comprises at least one sliding receptacle and the second housing part comprises at least one sliding guide rail or vice versa, wherein the sliding receptacle and the sliding guide rail in conjunction form a sliding connector configured for establishing a releasable mechanical connection between the first housing part and the second housing part.

Embodiment 26

The medical device according to the preceding embodiment, wherein the housing further comprises at least one latching mechanism, wherein the first housing part comprises at least one latching receptacle and the second housing part comprises at least one latching protrusion or vice versa, wherein latching receptacle is configured for receiving and fixing the latching protrusion.

Embodiment 27

The medical device according to any one of the two preceding embodiments, wherein the first sealing element and the second sealing element are arranged transverse to the sliding receptacle and the sliding guide rail.

Embodiment 28

The medical device according to any one of the three preceding embodiments, wherein the housing comprises at least one face side and at least one longitudinal side, wherein the first sealing element and the second sealing element are arranged along the face side and wherein the sliding receptacle and the sliding guide rail are arranged along the longitudinal side.

Embodiment 29

The medical device according to any one of the preceding embodiments, wherein one or both of the first material and the second material are selected from the group consisting of: a thermoplastic material, specifically a thermoplastic compound comprising polycarbonate and acrylonitrile butadiene styrene.

Embodiment 30

The medical device according to any one of the preceding embodiments, wherein at least one element selected from the group consisting of: the first housing part, the second housing part, the first sealing element, the second sealing element, is manufactured via injection molding.

Embodiment 31

The medical device according to any one of the preceding embodiments, wherein the first housing part and the first sealing element are manufactured as one piece.

Embodiment 32

The medical device according to any one of the preceding claims, wherein the second housing part and the second sealing element are manufactured as one piece.

Embodiment 33

The medical device according to any one of the preceding embodiments, wherein the housing comprises at least one battery compartment, wherein the first housing part and the second housing part are configured for enclosing the battery compartment.

Embodiment 34

The medical device according to the preceding embodiment, wherein the second housing part is a battery compartment lid.

Embodiment 35

The medical device according to any one of the preceding embodiments, wherein the medical device is selected from the group consisting of: a medical pump, specifically an insulin pump; a remote control unit of a medical pump; a handheld medical measurement device, specifically a handheld blood glucose measurement device.

Embodiment 36

A method for disassembling at least one medical device, the method comprising:

a) providing at least one medical device according to any one of the preceding embodiments, wherein the first housing part and the second housing part form the coupled state,
b) pushing the second housing part relative to the first housing part, thereby removing one or more of water, dust, dirt from a gap between the first housing part and the second housing part via the second sealing element.

Embodiment 37

A method for manufacturing at least one medical device, wherein the method comprises:

I. providing at least one first housing part, wherein the first housing part comprises at least one first sealing element, wherein the first housing part and the first sealing element are formed from a same first material, wherein the first sealing element forms at least one first protrusion;
II. providing at least one second housing part, wherein the second housing part comprises at least one second sealing element, wherein the second housing part and the second sealing element are formed from a same second material, wherein the second sealing element forms at least one second protrusion;
III. releasably coupling the first housing part and the second housing part to each other such that the first housing part and the second housing part form a coupled state.

Embodiment 38

The method according to the preceding embodiment, wherein the medical device corresponds to a medical device according to any one of the preceding embodiments referring to a medical device.

Embodiment 39

The method according to any one of the two preceding embodiments, wherein one or both of the first housing part, the second housing part, are manufactured via injection molding.

Embodiment 40

The method according to any one of the three preceding embodiments, wherein the first housing part and the first sealing element are manufactured as one piece.

Embodiment 41

The method according to any one of the four preceding embodiments, wherein the second housing part and the second sealing element are manufactured as one piece.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Figure 1:
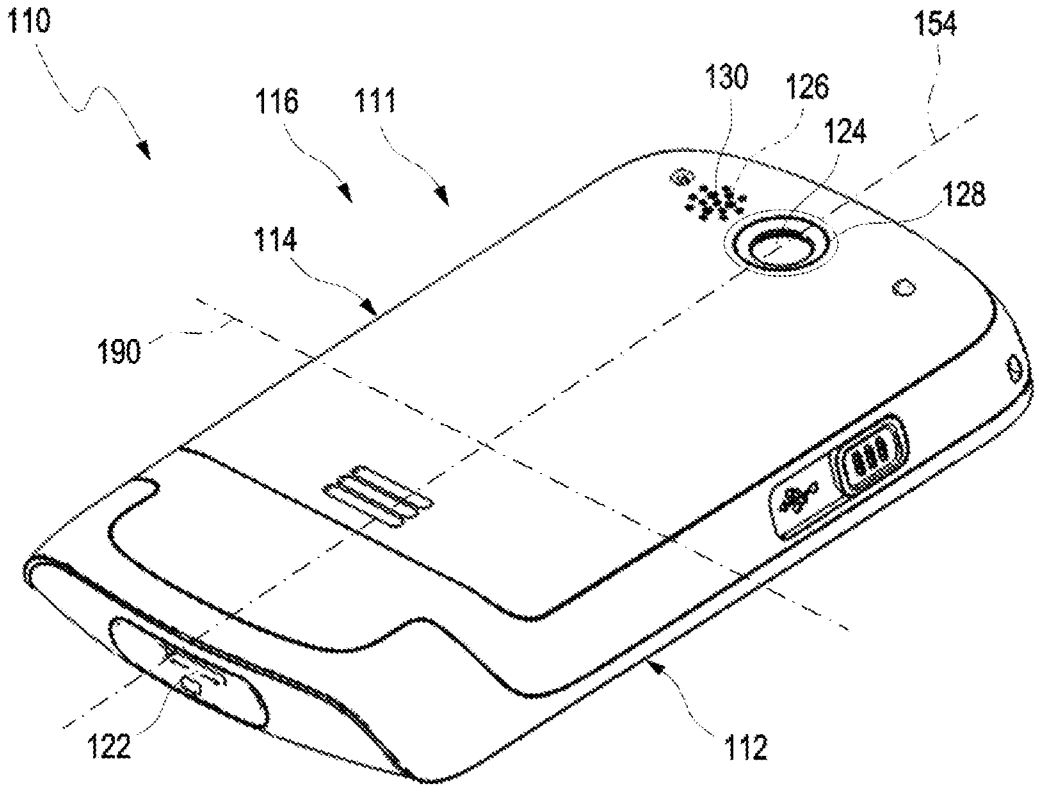
FIGS. 1A, 1B and 1C show an exemplary embodiment of a medical device in various perspective views.
FIGS. 1D and 1E show cross-sectional views of an exemplary embodiment of a medical device.
Figure 1:
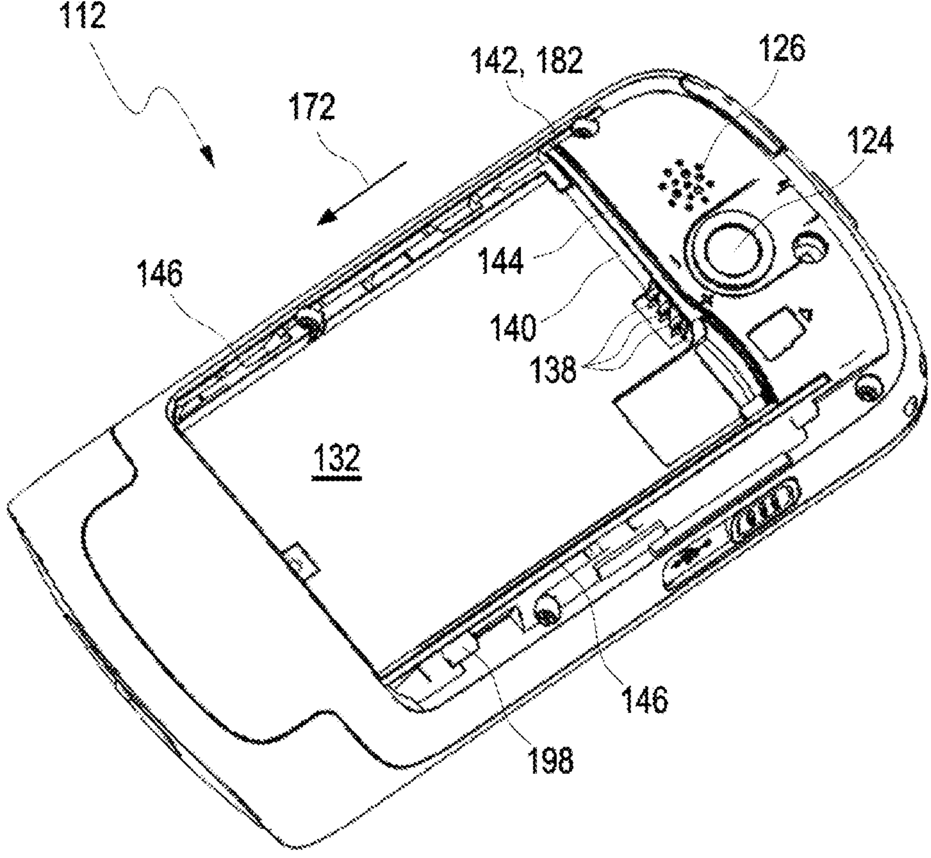
Figure 1:
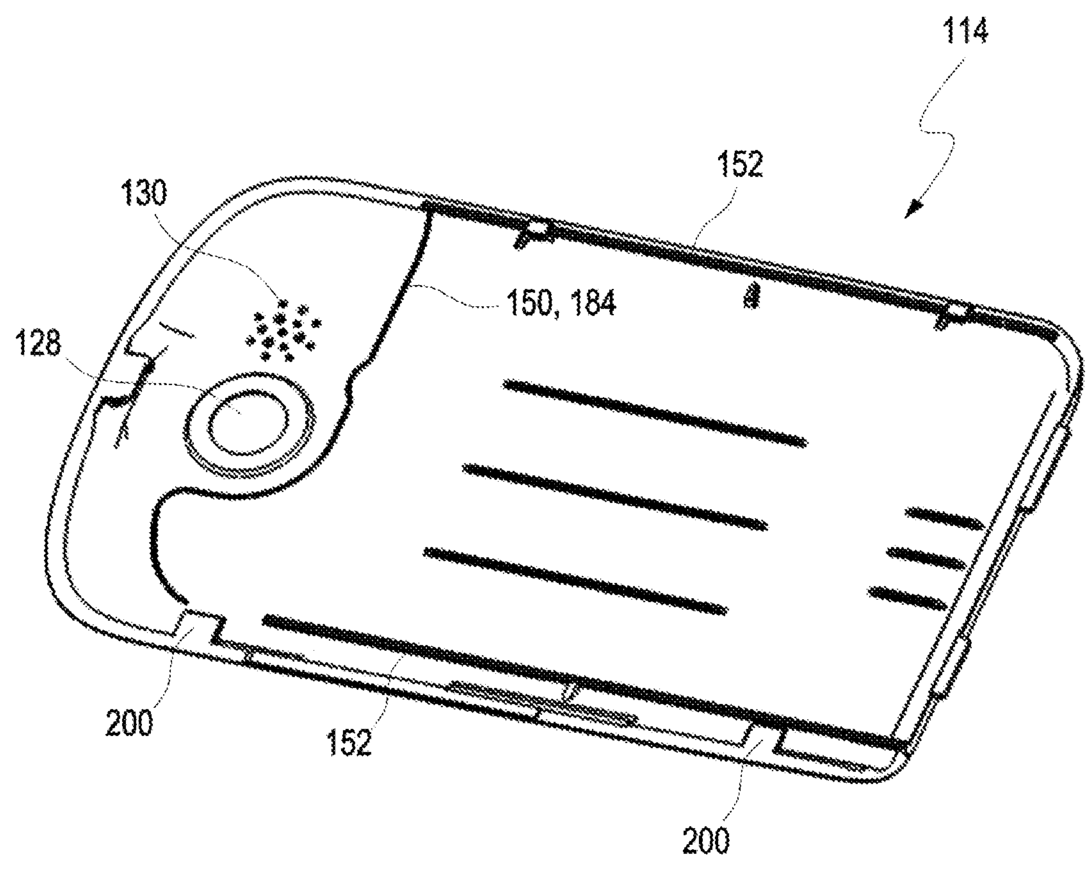
Figure 1:
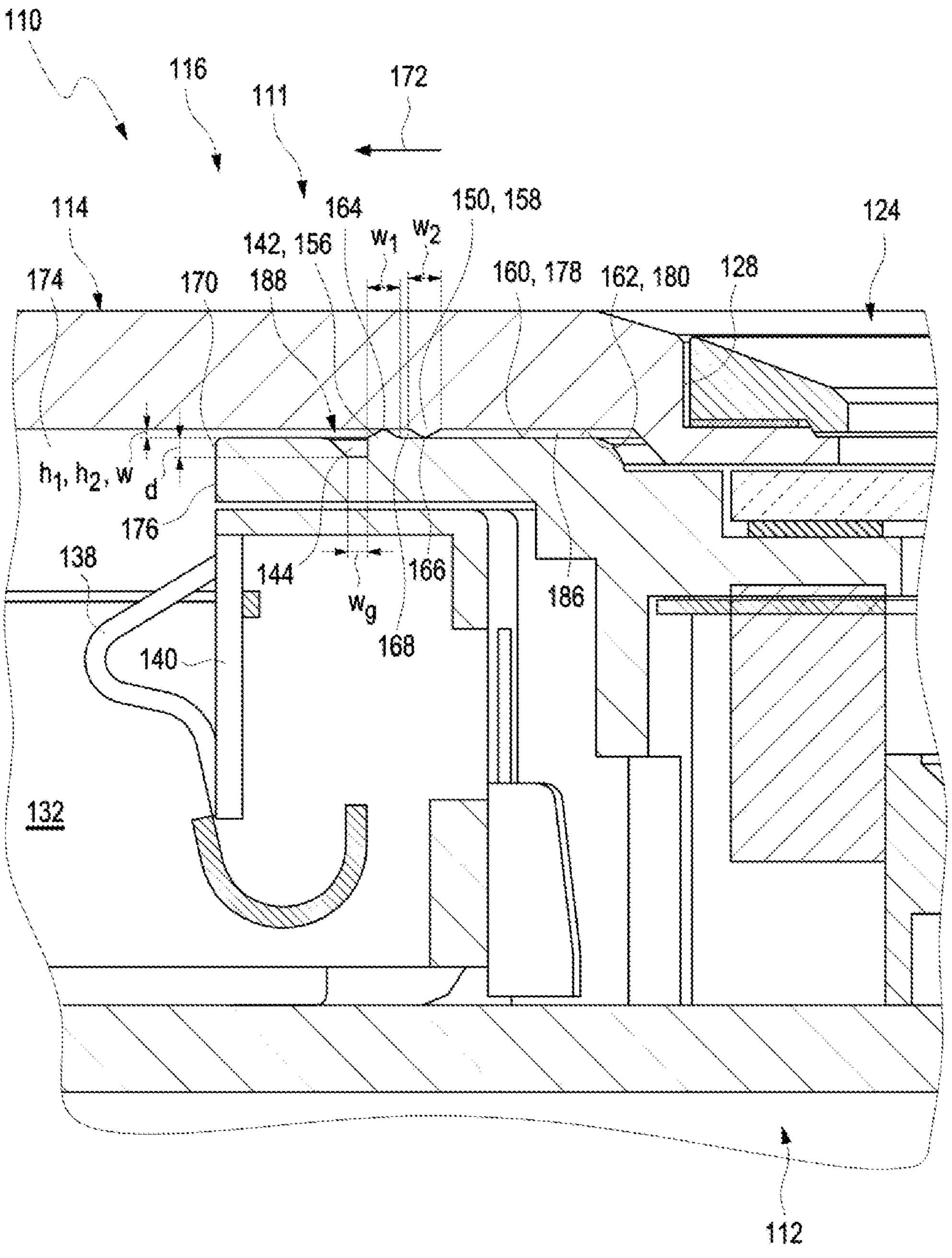
Figure 1:
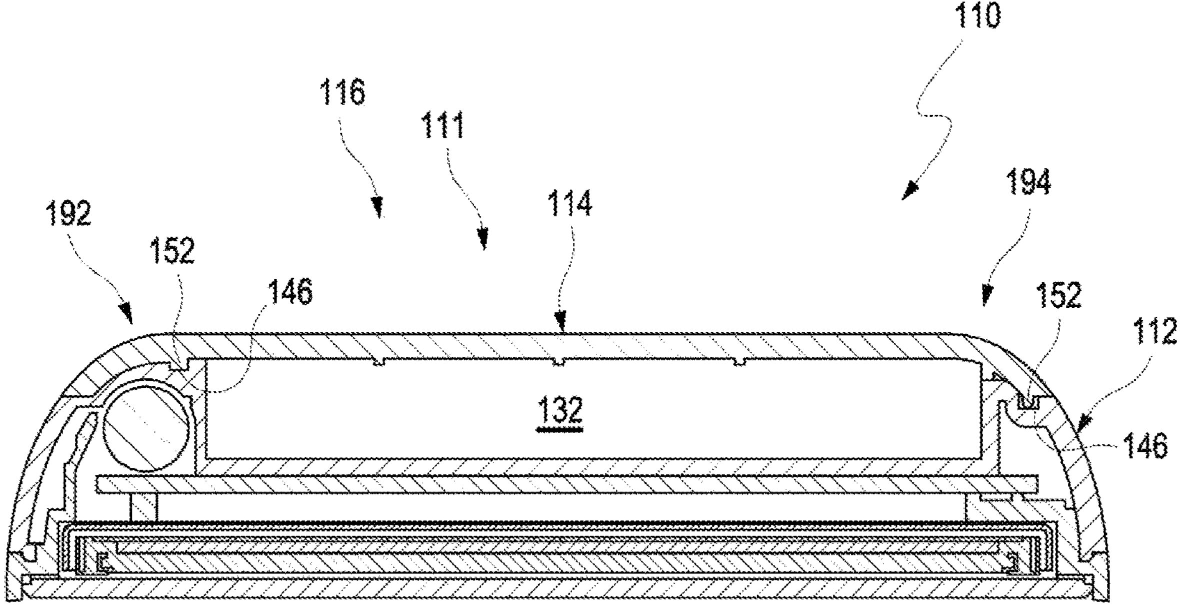

Corresponding reference characters indicate corresponding parts throughout the several views. Although the exemplification set out herein illustrates embodiments of the invention, in several forms, the embodiments disclosed are not intended to be exhaustive or to limit the invention to the precise forms disclosed in the present disclosure. Rather, the embodiments are chosen and described so that others skilled in the art may appreciate and understand the principles and practices of this disclosure.

DETAILED DESCRIPTION

FIGS. 1A to 1B show an exemplary embodiment of a medical device 110. In FIG. 1A, the medical device 110, specifically a housing 111 of the medical device 110, is shown in a perspective view. Thereby, a first housing part 112 and a second housing part 114 are shown in a coupled state 116. In the embodiment as illustrated in FIGS. 1A to 1E the medical device 110 may be a handheld medical measurement device, specifically a handheld blood glucose measurement device. The handheld medical measurement device may be configured to conduct at least one analytical measurement on a test field of a test element and to derive at least one item of information from the analytical measurement which relates to a health status of a user or a patient. For this purpose, the handheld medical measurement device may have a test element port 122 configured for receiving a test element (not shown) at least partially. The handheld medical measurement device may further comprise at least one camera 124 and at least one loudspeaker 126. Therefore, the handheld medical measurement device may have outlets 128, 130.

In FIG. 1B the first housing part 112 of the medical device 110 is shown in a perspective state. The housing 111, specifically the first housing part 112, may comprise at least one compartment 132, specifically at least one battery compartment. The battery compartment may be configured for receiving at least one electrical energy source such as a battery or an accumulator (not shown). The compartment 132 may be an open compartment configured for receiving the electrical component. The compartment 132 may comprise electrical contacts 138 in at least one sidewall 140 of the compartment 132 for contacting the electrical component.

The first housing part 112 further comprises at least one first sealing element 142. Moreover, the first housing part 112 may comprise at least one groove 144. Further details will be given below. Further, the first housing part 112 may comprise sliding receptacles 146. Again, further details will be given below.

In FIG. 1C the second housing part 114 of the medical device 110 is shown in a perspective state. The second housing part 114 may form a sliding lid of the housing 111. Specifically, the sliding lid may be releasably couplable to the first housing part 112. The sliding lid may be configured to cover the compartment 132 as depicted in FIG. 1B.

The second housing part 114 further comprises at least one second sealing element 150. Further details will be given below. Further, the second housing part 114 may comprise sliding guide rails 152. Again, further details will be given below.

FIG. 1D shows a cross-sectional view of a cross-section along a longitudinal axis 154 as illustrated in FIG. 1A. Thereby, the first housing part 112 and the second housing part 114 are in the coupled state 116. This cross-sectional view enables an enlarged view specifically on the first sealing element 142 and the second sealing element 150. The first sealing element 142 forms at least one first protrusion 156 and the second sealing element 150 forms at least one second protrusion 158.

The first housing part 112 and the first sealing element 142 are formed from a same first material and the second housing part 114 and the second sealing element 150 are formed from a same second material. The first material and/or the second material may, for example, be a thermoplastic compound comprising polycarbonate and acrylonitrile butadiene styrene. The first housing part 112 and/or the first sealing 142 element may be manufactured via injection molding. Specifically, the first housing part 112 and the first sealing element 142 may be manufactured as one piece and the second housing part 114 and the second sealing element 150 may be manufactured as one piece.

A cross-section of the first protrusion 156 and/or of the second protrusion 158 may be triangularly formed. The first protrusion 156 may extend from a surface 160 of the first housing part 112 and may be tapered. Thus, a first tip 164 of the first protrusion 156 may extend transverse, specifically perpendicular, from the surface 160 of the first housing part 112. The first tip 164 may point to a surface 162 of the second housing part 114 and may specifically be in direct contact with the surface 162 of the second housing part 114.

The second protrusion 158 may extend from the surface 162 of the second housing part 114. Thus, the second protrusion 158 may have a second tip 166 which extends transverse, specifically perpendicular, from the surface 162 of the second housing part 114.

The first protrusion 156 and/or the second protrusion 156 may, for example, have a width w1, w2 of 0.3 mm to 0.4 mm. Further, the first protrusion 156 and/or the second protrusion 158 may, for example, have a height h1, h2 of 0.1 mm to 0.2 mm.

In the coupled state 116 of the first housing part 112 and the second housing part 114 as illustrated in FIG. 1D, the first sealing element 142 of the first housing part 112 and the second sealing element 150 of the second housing part 114 may be arranged offset in relation to each other. Thus, the first sealing element 142 of the first housing part 112 and the second sealing element 150 of the second housing part 114 may form an intermediate space 168.

In the coupled state 116, the first and second sealing elements 142, 150 may be located at least on a side 170 of the compartment 132 adjacent to the side wall 140 having the electrical contacts 138. The second housing part 114 may be configured for being slid onto the first housing part 112 in a sliding direction 172. The sliding direction 172 may be at least essentially parallel to a longer side 174 of a rectangular shape of the compartment 132. Further, the first and second protrusions 156, 158 may be arranged on a side 176 upstream the rectangular shape with respect to the sliding direction 172.

Further, as can be seen in FIGS. 1B, 1C, and 1D in the coupled state 116 of the first housing part 112 and the second housing part 114 the first sealing element 142 and the second sealing element 150 may be arranged parallel to each other. As specifically illustrated in FIGS. 1B and 1C, the first sealing element 142 and/or the second sealing element 150 may respectively have a curved shape. The curved shape of the first sealing element 142 may correspond to the curved shape of the second sealing element 150.

As illustrated in FIG. 1D, the first housing part 112 may comprise at least one first sealing surface 178 and the second sealing element 150 may seal against the first sealing surface 178. Further, the second housing part 114 may comprise at least one second sealing surface 180 and the first sealing element 142 may seal against the second sealing surface 180.

As also illustrated in FIG. 1D, the first protrusion 156 may protrude from the first sealing surface 178 and the second protrusion 158 may protrude from the second sealing surface 180. The first protrusion 156 may seal against the second sealing surface 180 along at least one first sealing line 182 (illustrated in FIG. 1B) and the second protrusion 158 may seal against the first sealing surface 178 along at least one second sealing line 184 (illustrated in FIG. 1C). The first and second sealing lines 182, 184 may be offset from one another, as illustrated in FIG. 1D.

Further, the first and second sealing surfaces 178, 180 may be offset from one another, as illustrated in FIG. 1D, thereby forming a gap 186 between the first and second sealing surfaces 178, 180. The first protrusion 156 may protrude from the first sealing surface 178 by a first height h1 and the second protrusion 158 may protrude from the second sealing surface 180 by a second height h2. The first height h1 and the second height h2 may be equal. Further, a width w of the gap 186 may correspond to the first and second heights h1, h2.

The first housing part 112 may additionally comprise the groove 144, as illustrated in FIG. 1D. The groove 144 may be configured for collecting fluids. The groove 144 may, for example, have a width $w_g$ of 0.5 mm to 0.7 mm. Further, the groove 144 may, for example, have a depth d of 0.2 mm to 0.3 mm. The groove 144 may be arranged on the surface 160 of the first housing part 112. Thus, the groove 144 may be arranged adjacent to the first sealing element 142. Further, the groove 144 may be arranged adjacent to the intermediate space 168 formed by the first sealing element 142 and the second sealing element 150. The first housing part 112 and the second housing part 114, in the coupled state 116, may enclose the intermediate space 168 and the groove 144 may be arranged on a side 188 of the first and second sealing elements 142, 150 facing towards the intermediate space 168.

FIG. 1E shows a cross-sectional view of a cross-section along a short axis 190 as illustrated in FIG. 1A.

The housing 111 may comprise at least one linear sliding mechanism 192. The first housing part 112 may comprise the at least one sliding receptacle 146 and the second housing part 114 may comprise the at least one sliding guide rail 152. The sliding receptacle 146 and the sliding guide rail 152 in conjunction may form a sliding connector 194 configured for establishing a releasable mechanical connection between the first housing part 112 and the second housing part 114. For example, the sliding guide rail 152 may be formed as a protrusion 196. The sliding guide rail 152 and the sliding receptacle 146 may be shaped complementary to each other. The first housing part 112 and the second housing part 114 may be configured to establish at least one mechanical connection, specifically a form-fit connection.

The housing 111 may further comprise at least one latching mechanism. The first housing part 112 may comprise at least one latching receptacle 198, as illustrated in FIG. 1B, and the second housing part 114 may comprise at least one latching protrusion 200. The latching receptacle 198 may be configured for receiving and fixing the latching protrusion 200. Thus, the latching protrusion 200 may be removable from the latching receptacle 198 by applying a force to the second housing part 114 relative to the first housing part 112 in the sliding direction 172. However, when applying a force to the second housing part 114 in a counter direction, a movement of the second housing part 114 relative to the first housing part 12 may be blocked.

While this invention has been described as having an exemplary design, the present invention may be further modified within the spirit and scope of this disclosure. This application is therefore intended to cover any variations, uses, or adaptations of the invention using its general principles.

LIST OF REFERENCE NUMBERS

110 medical device
111 housing
112 first housing part
114 second housing part
116 coupled state
122 test element port
124 camera
126 loudspeaker
128 outlet
130 outlet
132 compartment
138 electrical contacts
140 sidewall
142 first sealing element
144 groove
146 sliding receptacle
150 second sealing element
152 sliding guiderail
154 longitudinal axis
156 first protrusion
158 second protrusion
160 surface
162 surface
164 first tip
166 second tip
168 intermediate space
170 side
172 sliding direction
174 longer side
176 side
178 first sealing surface
180 second sealing surface
182 first sealing line
184 second sealing line
186 gap
188 side
190 short axis
192 linear sliding mechanism
194 sliding connector
198 latching receptacle
200 latching protrusion

What is claimed is:

1. A medical device having a housing, wherein the housing comprises:
- a first housing part having a first sealing element;
- a second housing part having a second sealing element;
- wherein the first housing part and the second housing part are releasably couplable to each other and are configured to form a coupled state;
- wherein the first housing part and the first sealing element are formed from a same first material;
- wherein the second housing part and the second sealing element are formed from a same second material;
- wherein the first sealing element forms a first protrusion;
- wherein the second sealing element forms a second protrusion;
- wherein the first housing part comprises a first sealing surface, the second housing part comprises a second sealing surface and, in the coupled state, the first sealing element seals against the second sealing surface along a first sealing line and the second sealing element seals against the first sealing surface along a second sealing line;
- wherein the housing includes a linear sliding mechanism, the linear sliding mechanism having a sliding receptacle disposed on one of the first and second housing parts and a sliding guide rail disposed on the other one of the first and second housing parts wherein the sliding receptacle and the sliding guide rail together form a sliding connector configured for establishing a releasable mechanical connection between the first housing part and the second housing part wherein the second housing part forms a sliding lid of the housing; and
- the first protrusion and the second protrusion each have a width and a height, wherein the first protrusion extends along the first sealing surface and the second protrusion extends along the second sealing surface and wherein the first protrusion, the first sealing line, the second protrusion and the second sealing line all extend transverse to a sliding direction of the second housing part and wherein the housing includes at least one face side and at least one longitudinal side wherein the first sealing element and the second sealing element are arranged along the face side and the sliding receptacle and the sliding guide rail are arranged along the longitudinal side.

2. The medical device according to claim 1 wherein the first protrusion seals against the second sealing surface along a first sealing line, the second protrusion seals against the first sealing surface along a second sealing line, and the first sealing line and the second sealing line are offset from one another.

3. The medical device according claim 1 wherein the first sealing surface and the second sealing surface are offset from one another thereby forming a gap between the first sealing surface and the second sealing surface wherein moving the second housing part relative to the first housing part clears fluids, dust and dirt within the gap with the second sealing element and thereby prevents the fluids, dust and dirt from reaching an interior compartment of the housing.

4. The medical device according to claim 3 wherein the first protrusion protrudes from the first sealing surface by a first height $h_1$, the second protrusion protrudes from the second sealing surface by a second height $h_2$, and the first height $h_1$, the second height $h_2$, and the width w of the gap are all equal to each other.

5. The medical device according to claim 1 wherein, in the coupled state, an intermediate space is formed between the first sealing element of the first housing part and the second sealing element of the second housing part.

6. The medical device according to claim 1 wherein, in the coupled state, the first sealing element and the second sealing element are arranged parallel to each other.

7. The medical device according to claim 1 wherein the first housing part contains an open compartment configured to receive at least one electrical component, and the second housing part, in the coupled state, covers the open compartment.

8. The medical device of claim 1 further comprising a latching mechanism wherein one of the first housing part and the second housing part comprises a latching receptacle and the other of the first housing part and the second housing part comprises a latching protrusion, the latching receptacle being configured to receive and releasably secure the latching protrusion when the first housing part and the second housing part are releasably coupled to each other in the coupled state.

9. The medical device according to claim 1 wherein the first housing part contains an open compartment configured to receive at least one electrical component and having a rectangular shape, and the second housing part, in the coupled state, covers the open compartment and wherein a sliding direction of the linear sliding mechanism is parallel to a longer side of the rectangular shape of the compartment and the first protrusion and the second protrusion are arranged on a side upstream of the rectangular shape of the compartment with respect to the sliding direction.

10. A method for disassembling a medical device, the method comprising:

(a) providing a medical device according to claim 1 wherein the first housing part and the second housing part are in the coupled state; and (b) pushing the second housing part relative to the first housing part and thereby removing one or more of water, dust, or dirt from a gap between the first housing part and the second housing part with the second sealing element.

11. A medical device having a housing, wherein the housing comprises:

a first housing part having a first sealing element;

a second housing part having a second sealing element;

wherein the first housing part and the second housing part are releasably couplable to each other and are configured to form a coupled state;

wherein the first housing part and the first sealing element are formed from a same first material;

wherein the second housing part and the second sealing element are formed from a same second material;

wherein the first sealing element forms a first protrusion protruding from and extending along a flat surface on the first housing part;

wherein the second sealing element forms a second protrusion protruding from and extending along a flat surface on the second housing part;

wherein, when the first housing part and the second housing part form the coupled state, the first sealing element seals against the flat surface on the second housing part along a first sealing line and the second sealing element seals against the flat surface on the first housing part along a second sealing line;

wherein the first housing part or the second housing part define a groove configured for collecting fluids and wherein the groove forms a recess in the flat surface of the first housing part or the flat surface of the second housing part and is adjacent to one or both of the first protrusion and the second protrusion;

wherein one of the first and second sealing elements is engageable with the flat surface in which the recess is formed and is not projectable into the recess;

wherein, when the first housing part and the second housing part form the coupled state, the recess is disposed adjacent an intermediate space between the first sealing element and the second sealing element and faces one of the flat surfaces on the first and second housing parts;

wherein the housing includes a linear sliding mechanism, the linear sliding mechanism comprising a sliding receptacle disposed on one of the first housing part and the second housing part and a sliding guide rail disposed on the other one of the first housing part and second housing part wherein the sliding receptacle and the sliding guide rail together form a sliding connector configured for establishing a releasable mechanical connection between the first housing part and the second housing part wherein the second housing part forms a sliding lid of the housing; and wherein the first protrusion and the second protrusion each have a width and a height, wherein the first protrusion, the first sealing line, the second protrusion and the second sealing line all extend transverse to a sliding direction of the linear sliding mechanism and wherein pushing the second housing part relative to the first housing part in the coupled state removes one or more of water, dust and dirt from a gap between the first housing part and the second housing part via the second sealing element.

12. The medical device according to claim 11 wherein the first housing part contains an open compartment configured to receive at least one electrical component and having a rectangular shape, and the second housing part, in the coupled state, covers the open compartment and wherein a sliding direction of the linear sliding mechanism is parallel to a longer side of the rectangular shape of the compartment and the first protrusion and the second protrusion are arranged on a side upstream of the rectangular shape of the compartment with respect to the sliding direction.

13. A method for assembling a medical device, the method comprising:

(I) providing a first housing part having a first sealing element wherein the first housing part and the first sealing element are formed from a same first material and wherein the first sealing element forms at least one first protrusion;

(II) providing a second housing part having a second sealing element wherein the second housing part and the second sealing element are formed from a same second material and wherein the second sealing element forms at least one second protrusion;

(III) releasably coupling the first housing part and the second housing part to each other such that the first housing part and the second housing part form a coupled state; wherein the first housing part comprises a first sealing surface, the first sealing surface being a flat surface, wherein, in the coupled state, the second sealing element seals against the first sealing surface along a second sealing line; and wherein the second housing part comprises a second sealing surface, the second sealing surface being a flat surface, wherein, in the coupled state, the first sealing element seals against the second sealing surface along a first sealing line; and wherein the housing includes a linear sliding mechanism having a sliding receptacle disposed on one of the first housing part and the second housing part and a sliding guide rail disposed on the other one of the first housing part and the second housing part wherein the sliding receptacle and the sliding guide rail together form a sliding connector configured for establishing a releasable mechanical connection between the first housing part and the second housing part, wherein the second housing part forms a sliding lid of the housing and the first protrusion and the second protrusion each have a width and a height, wherein the first protrusion, the first sealing line, the second protrusion and the second sealing line all extend transverse to a sliding direction of the linear sliding mechanism.

14. The method according to claim 13 wherein one or both of the first housing part and the second housing part are manufactured using injection molding.

15. The method according to claim 13 wherein the first housing part and the first sealing element are manufactured as one piece and the second housing part and the second sealing element are manufactured as one piece.

16. The method of claim 13 wherein the housing includes at least one face side and at least one longitudinal side wherein the first sealing element and the second sealing element are arranged along the face side and the sliding receptacle and the sliding guide rail are arranged along the longitudinal side.

17. The method of claim 13 wherein a cross-section of the first protrusion along the sliding direction and a cross-section of the second protrusion along the sliding direction both define a triangular shape.

* * * * *